(12) United States Patent
Ivachtchenko et al.

(10) Patent No.: US 9,428,491 B2
(45) Date of Patent: Aug. 30, 2016

(54) SUBSTITUTED AZOLES, ANTIVIRAL ACTIVE COMPONENT, PHARMACEUTICAL COMPOSITION, METHOD FOR PREPARATION AND USE THEREOF

(76) Inventors: Alexandre Vasilievich Ivachtchenko, Encinitas, CA (US); Vadim Vasilievich Bichko, San Diego, CA (US); Oleg Dmitrievich Mitkin, Khimki (RU)

( * ) Notice: Subject to any disclaimer, the term of this patent is extended or adjusted under 35 U.S.C. 154(b) by 0 days.

(21) Appl. No.: 13/990,428

(22) PCT Filed: Nov. 28, 2011

(86) PCT No.: PCT/RU2011/000932
§ 371 (c)(1),
(2), (4) Date: May 30, 2013

(87) PCT Pub. No.: WO2012/074437
PCT Pub. Date: Jun. 7, 2012

(65) Prior Publication Data
US 2013/0253008 A1    Sep. 26, 2013

(30) Foreign Application Priority Data
Nov. 30, 2010 (RU) .................. 2010148813

(51) Int. Cl.
C07D 403/14 (2006.01)
C07D 403/04 (2006.01)
C07D 409/14 (2006.01)
C07D 405/14 (2006.01)
C07D 413/14 (2006.01)

(52) U.S. Cl.
CPC ........... *C07D 403/14* (2013.01); *C07D 403/04* (2013.01); *C07D 405/14* (2013.01); *C07D 409/14* (2013.01); *C07D 413/14* (2013.01)

(58) Field of Classification Search
CPC  C07D 403/04; C07D 503/14; C07D 405/14; C07D 409/14; C07D 413/14; C07D 403/14
USPC ......... 514/316, 374, 397; 546/187; 548/235, 548/313.1, 314.7
See application file for complete search history.

(56) References Cited

U.S. PATENT DOCUMENTS 8,088,368 B2 * 1/2012 Guo et al. .................. 424/85.4
8,329,159 B2 * 12/2012 Belema et al. ............. 424/85.2
8,637,561 B2 * 1/2014 Qiu et al. .................... 514/398

OTHER PUBLICATIONS

Im proper Markush, Fed. Reg. vol. 76 (27) 7162-7175, slide 1, 64-67 (2011).*
Ei-Subbagh et al. "2,3-disubstituted . . . " Eur. J. Med. Chem. v. 31 p. 1017-1021 (1996).*
New Matter "The USPTO connection" p. 1-3, (2005).*
Ivashchenko et al. "substituted azoles . . . " CA157:77078 (2012).*

* cited by examiner

*Primary Examiner* — Celia Chang

(57) ABSTRACT

The present invention relates to novel antiviral active 5-{4-[1H-imidazol-5-ylaryl(or hetaryl)]-buta-1,3-diynyl}-1H-imidazoles of the general formula 1 and pharmaceutically acceptable salt thereof, pharmaceutical composition, antiviral medicament, therapeutic kit for prophylaxis and treatment of hepatisis C virus diseases, and method for prophylaxis and treatment of hepatisis C.

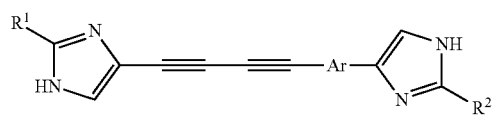

wherein:
$R^1$ and $R^2$—represent optionally identical radicals selected from 2.1 and 2.2, where an asterisk (*) denotes the position of attachment to the imidazole fragment, (S) and (R) are types of chiral centers;

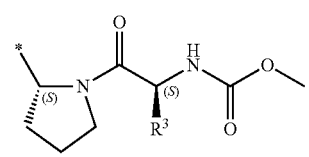

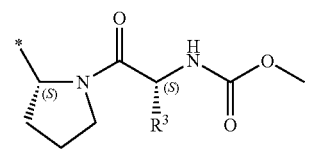

$R^3$ is isopropyl or phenyl radicals;
Ar an aromatic or heteroaromatic diradical.

3 Claims, No Drawings

SUBSTITUTED AZOLES, ANTIVIRAL ACTIVE COMPONENT, PHARMACEUTICAL COMPOSITION, METHOD FOR PREPARATION AND USE THEREOF

CROSS REFERENCE TO RELATED APPLICATIONS

This application is a National stage of International application PCT/RU2011/000932 filed Nov. 28, 2011, which claims benefit of foreign priority to the Russian Federation application RU 2010148813 of Nov. 30, 2010. The priority applications are hereby incorporated by reference in their entirety.

FIELD OF THE INVENTION

The present invention relates to novel azoles, novel antiviral active component, pharmaceutical composition, antiviral medicament, method for prophylaxis and treatment of viral diseases, particularly caused by hepatitis C viruses (HCV).

PRIOR ART

Virus infections may cause a great number of diseases that creates a serious threat for health and existence of mankind. For the last 20 years not less than 30 essentially new infectious agents have been discovered such as: HIV, viral hepatitises, acute and long-lasting diarrhea, hemorrhagic fever (Ebola, Venezuelan, Brazilian, Rift valleys) [a) Lednicky J. A., Rayner J. O. Uncommon respiratory pathogens. Curr. Opin. Pulm. Med. 2006, 12(3), 235-239. b) Hayden F. G. Respiratory viral threats. Curr. Opin. Infect. Dis. 2006, 19(2), 169-178]. According to statistical data 60-65% of epidemic infections have viral ethiology. Because of the complexity of interaction in triad "virus—host's organism—drug", most of modern antiviral drugs lead to side effects in the course of therapy and form resistant virus strains [Jain R., Clark N. M., Diaz-Linares M., Grim S. A. Limitations of current antiretroviral agents and opportunities for development. *Curr. Pharm. Des.* 2006, 12(9), 1065-1074.]. At present, the number of antiviral drugs that may be used in clinical practice is extremely limited—only 43 low molecular weight substances [http://integrity.prous.com/integrity], that is far from satisfying the requirements of prophylaxis and treatment of virus diseases. Moreover, there are a lot of virus infections causing diseases for treatment of which there are no chematherapeutic agents. It concerns, for example, to the diseases caused by viruses of papilloma, adenoviruses, herpes-6, variola, syndrome SARS, hemorrhagic fevers, Western Nile fever, avian influenza and so on. [De Clercq E. Recent highlights in the development of new antiviral drugs. *Curr Opin Microbiol.* 2005, 8(5), 552-560].

Hepatitis C virus falls into the category of Flaviviruses (genus Flaviviridae), together with other important human pathogens, such as yellow fever virus, West Nile virus, Dengue virus and hepatitis GBV-C virus. Flaviviruses possess similar genom structure, including genom coding non-structural NS5A protein. Being a structural component of virus replication complex NS5A plays important role in virus RNA-genom replication. As far as this protein has been validated now in clinical trials as a target for design of medicaments for treating long-lasting hepatitis C, NS5A is considered to be a promising target for other listed above clinically important Flaviviruses as well.

Thus, the development of novel antiflavivirus medicaments, especially possessing high activity and low toxicity is of great importance now.

There are some publications in patent literature, dedicated to various derivatives of 2-pyrrolidin-2-yl-1H-imidazoles, which are ligands of non-structural protein NS5A and suppress hepatitis C virus (HCV) [WO 2008021927A2, WO 2009020825A1, WO 2009020828A1, WO 2010065668A1, WO2010065681A1, WO2010096302A1, WO2010096462A1, WO2010096777A1, WO2010111534A1, WO2010111673A1, WO2010117635A1, WO2010117977A1].

However, now searching of novel medicaments exhibiting high antiflavivirus efficiency is still one of the principal directions in the developing of new pharmacological agents for treating vide and diversified types of viral infections, including HCV.

In this context, synthesis of new compounds and putting them to use as antiviral active components, including HCV, for pharmaceutical compositions and medicament is of high priority.

DISCLOSURE OF THE INVENTION

In context of the invention, terms are generally defined as follows:

"Aryl" means aromatic mono- or polycyclic system with 6-14 carbon atoms, predominantly 6-10 carbon atoms. Aryl may have one or more "cyclic system substituents" of the same or different structure. Phenyl or naphthyl, substituted phenyl or substituted naphthyl are the representatives of aryl groups. Aryl may be annelated with nonaromatic cyclic system or heterocycle.

"Biradical" means a radical derived at removal of two hydrogen atoms from two C—H bonds of the molecule.

"Active component" (drug-substance) means a physiologically active compound of synthetic or other (biotechnological, vegetable, animal, microbe and so on) origins exhibiting pharmacological activity which is an active ingredient of pharmaceutical composition which is employed in production and preparation of medicaments.

"Medicament"—is a compound (or mixture of compounds in the form of pharmaceutical composition) in the form of tablets, capsules, injections, ointments and other ready forms intended for restoration, improvement or modification of physiological functions at humans and animals, and for treatment and prophylaxis of diseases or diagnostics, anesthesia, contraception, cosmetology and others.

"Therapeutic kit" is a simultaneously administered combination of two or more drug substances with different mechanism of pharmacological action and aimed at different biotargets taking part in pathogenesis of the disease.

"Pharmaceutical composition" means a composition comprising a compound of general formula 1 and at least one of components selected from group consisting of pharmaceutically acceptable and pharmacologicaly compatible excipients, solvents, diluents, carriers, auxiliary, distributing and sensing agents, delivery agents, such as preservatives, stabilizers, excipients, disintegrators, moisteners, emulsifiers, suspending agents, thickeners, sweeteners, flavouring agents, aromatizing agents, antibacterial agents, fungicides, lubricants, and prolonged delivery controllers, choice and suitable proportions of which depend on nature and way of administration and dosage. Examples of suitable suspending agents are ethoxylated isostearyl alcohol, polyoxyethene, sorbitol and sorbitol ether, microcrystalline cellulose, aluminum metahydroxide, bentonite, agar-agar and tragacant and their mixtures as well. Protection against the action of microorganisms can be provided by various antibacterial and antifungal agents, such as, for example, parabens, chlorobutanole, sorbic acid, and similar compounds. Composition may also contain isotonic agents, such as, for example, sugar, sodium chloride, and similar compounds. Prolonged effect of composition may be achieved by agents slowing down absorption of active ingredient, for example, aluminum monostearate and gelatine. Examples of suitable carriers, solvents, diluents and delivery agents include water, ethanol, polyalcohols and their mixtures, natural oils (such as olive oil) and organic esters (such as ethyl oleate) for injections. Examples of excipients are lactose, milk-sugar, sodium citrate, calcium carbonate, calcium phosphate and the like. Examples of disintegrators and distributors are starch, alginic acid and its salts, and silicates. Examples of suitable lubricants are magnesium stearate, sodium lauryl sulfate, talc and high molecular weight polyethylene glycol. Pharmaceutical composition for peroral, sublingval, transdermal, intramuscular, intravenous, subcutaneous, local or rectal administration of active ingredient, alone or in combination with another active compound may be administered to humans and animals in standard administration form, or in mixture with traditional pharmaceutical carriers. Suitable standard administration forms include peroral forms such as tablets, gelatin capsules, pills, powders, granules, chewing-gums and peroral solutions or suspensions, sublingval and transbuccal administration forms; aerosols; implants; local, transdermal, subcutaneous, intramuscular, intravenous, intranasal or intraocular forms and rectal administration forms.

"Pharmaceutically acceptable salt" means relatively non-toxic both organic and inorganic salts of acids and bases disclosed in this invention. Salts could be prepared in situ in processes of synthesis, isolation or purification of compounds or they could be prepared specially. In particular, bases salts could be prepared starting from purified base of disclosed compound and suitable organic or mineral acid. Examples of salts prepared in this manner include hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulphonates, malonates, salicylates, propionates, ethane sulphonates, benzene sulfonates, sulfamates and the like (Detailed description of properties of such salts is given in: Berge S. M., et al., "Pharmaceutical Salts" J. Pharm. Sci., 1977, 66: 1-19). Salts of disclosed acids may be also prepared by reaction of purified acids specifically with suitable base; moreover, metal salts and amine salts may be synthesized too. Metal salts are salts of sodium, potassium, calcium, barium, zinc, magnesium, lithium and aluminum, sodium and potassium salts being preferred. Suitable inorganic bases from which metal salts can be prepared are sodium hydroxide, carbonate, bicarbonate and hydride; potassium hydroxide, carbonate and bicarbonate, lithium hydroxide, calcium hydroxide, magnesium hydroxide, zinc hydroxide. Organic bases suitable for preparation of the disclosed acid salts are amines and amino acids of the sufficient basicity to produce a stable salt and suitable for use for medical purposes (in particular, they are to have low toxicity). Such amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl) aminomethane and the like. Besides, salts can be prepared using some tetraalkylammonium hydroxides, such as, for example, holine, tetramethylammonium, tetraethylammonium, and the like. Aminoacids may be selected from the main aminoacids-lysine, ornithine and agrinine.

The subject of the present invention is novel substituted 5-{4-[1H-imidazol-5-ylaryl(or hetaryl)]-buta-1,3-diynyl}-1H-imidazole of the general formula 1 and pharmaceutically acceptable salt thereof,

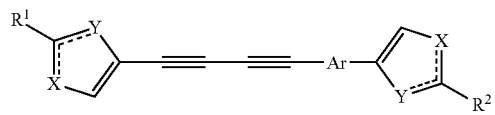

1 wherein:

solid lines with accompanying dotted lines (---) represent ordinary bond or double bond, provided that one of them is an ordinary bond, the other one is double bond;

X and Y optionally accept different meanings and represent nitrogen or NH group;

$R^1$ and $R^2$—represent optionally identical radicals selected from 2.1 and 2.2, where an asterisk (*) denotes the position of attachment to the imidazole fragment;

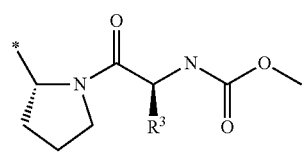

2.1

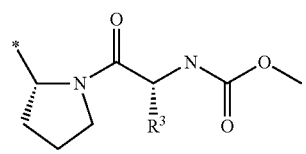

2.2

$R^3$ is isopropyl or phenyl radicals;

Ar is an aromatic or hetero aromatic diradical.

The best results are achieved if Ar is benzene biradical, naphtalene biradical, thiophene biradical, and thieno[3,2-b] thiophene biradical.

The subject of the present invention is novel substituted 5-{4-[1H-imidazol-5-ylaryl(or hetaryl)]-buta-1,3-diynyl}-1H-imidazole of the general formulas 1 selected from a number of 1.1-1.10 and pharmaceutically acceptable salt thereof, buta-1,3-diynyl}-1H-imidazole of formulae 1.1-1.10 and pharmaceutically acceptable salt thereof, 1.1
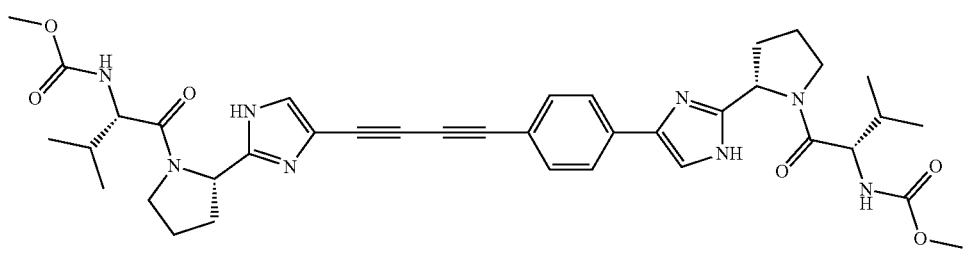
1.2
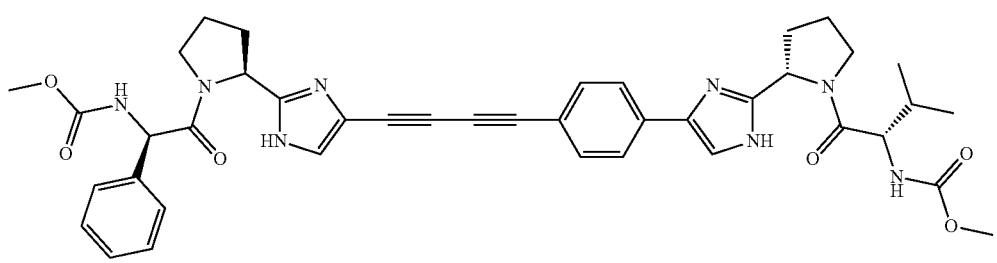
1.3
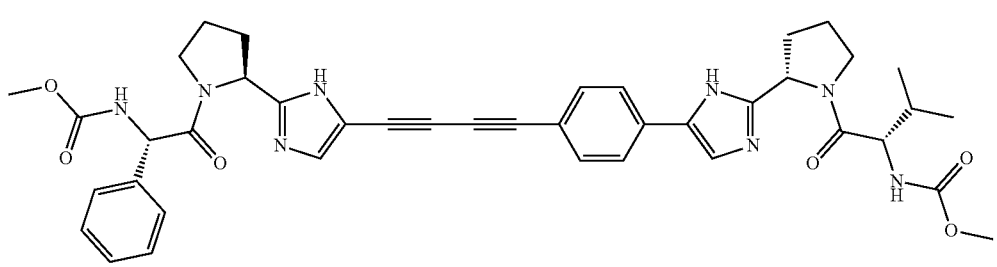
1.4
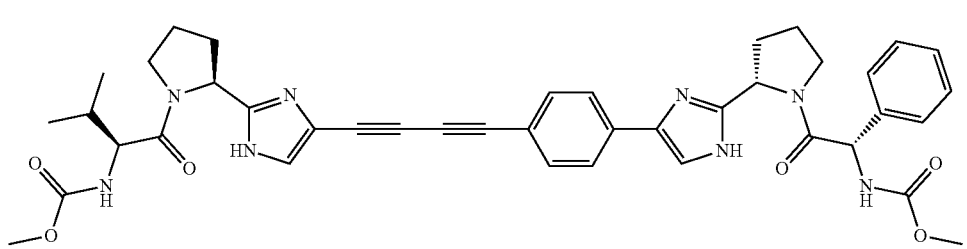
1.5
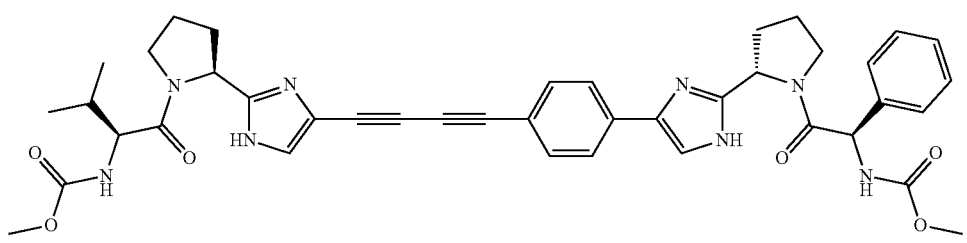
1.6
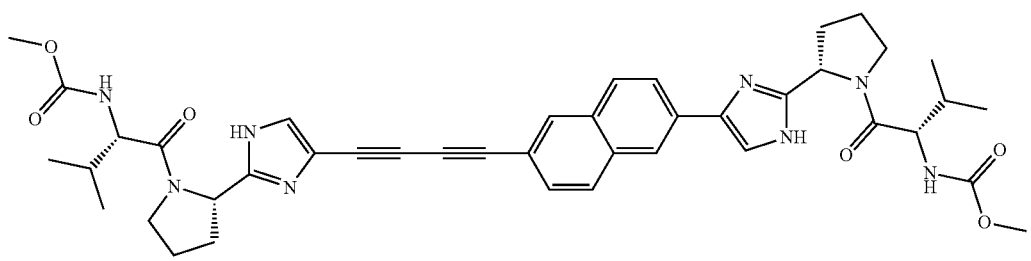

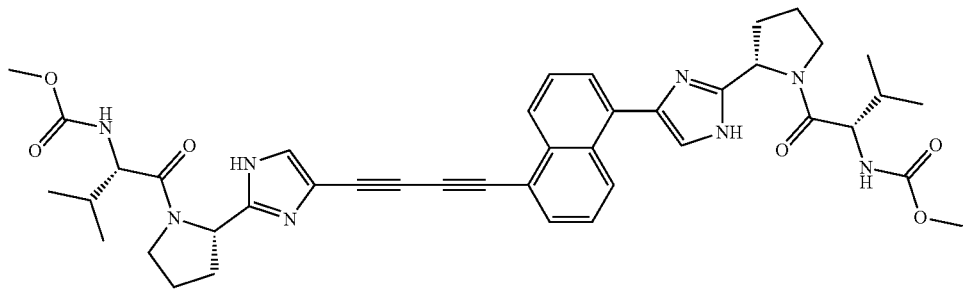

1.7

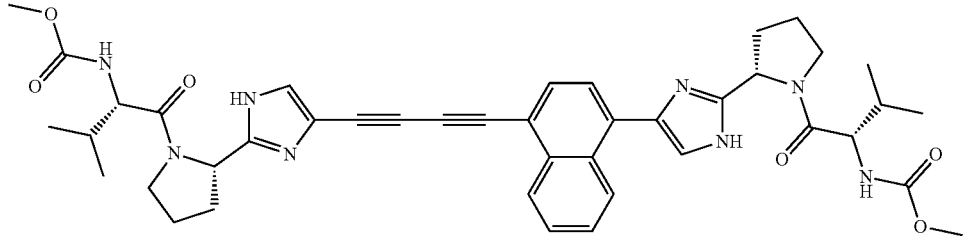

1.8

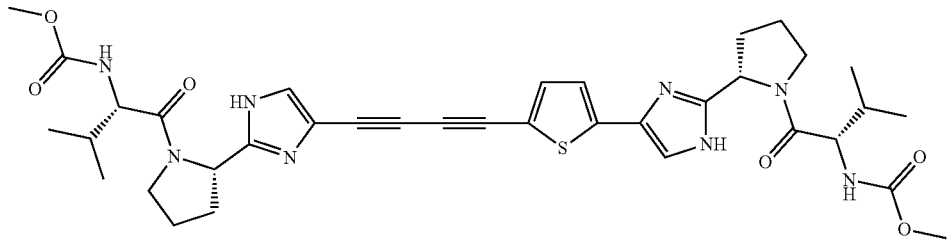

1.9

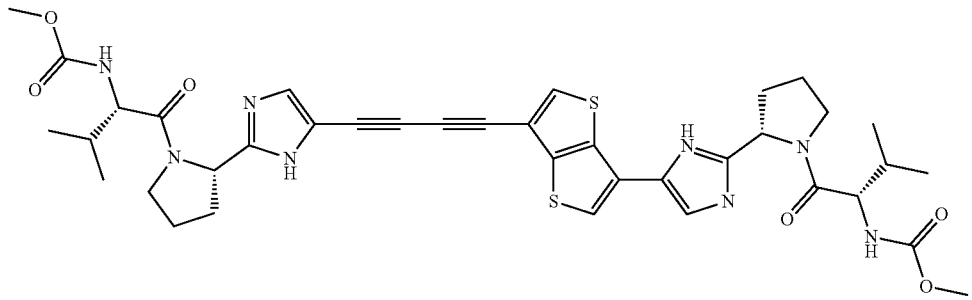

1.10

According to the invention substituted azoles of the general formulas 1 were prepared using known chemical reactions and commercial reagents. Structure of the compounds prepared was confirmed by LCMS and NMR data. The compounds were named using Chem Draw (Chembridge Soft Inc.) programme.

The following abbreviations were used in the schemes: DIPEA—diisopropylethylamine, EDAC—N-(3-dimethylaminopropyl)-N'-ethylcarbodiimide hydrochloride, HOBt—1-hydroxybenzotriazole, N-Boc-L-Pro-OH—N-(tert-butoxycarbonyl)-L-proline, N-Moc-L-Val-OH=N-(methoxycarbonyl)-L-valine, RP HPLC—reverse-phase high performance liquid chromatography, HPLC—high-performance liquid chromatography, DCM—dichloromethane, DMF—N,N-dimethylformamide, PdCl2dppf—[1,1'-bis(diphenylphosphino)ferrocene]dichloropalladium(II), TBTU—O-(benzotriazol-1-yl)-N,N,N',N'-tetramethyluronium tetrafluoroborate, DBU—1,8-diazabicyclo[5.4.0]undec-7-ene, SEM—2-trimethylsilanyl-ethoxymethyl, HCV—hepatitis C virus, DMEM—Dulbecco's Modified Eagle Medium—culture medium.

Preparation of NS5A inhibitors 1.1-1.5 which include buta-1,3-diynyl-benzene moiety is presented below on the following three synthetic schemes.

Thus, [(1S)-1-[[(2S)-2-[5-[4-[4-[2-[(2S)-1-[(2S)-2-[(methoxycarbonyl)amino]-3-methyl-1-oxobutyl]-2-pyrrolidinyl]-1H-imidazol-5-yl]-1,3-butadiynyl]phenyl]-1H-imidazol-2-yl]-1-pyrrolidinyl]carbonyl]-2-methylpropyl]-carbamic acid methyl ester 1.1 was obtained by starting from 2-((S)-1-Boc-pyrrolidin-2-yl)-5-(4-iodophenyl)-1H-imidazole (3.1) according to the following scheme. In this scheme, the key step is Sonogashira cross-coupling reaction between 2-((S)-1-Boc-pyrrolidin-2-yl)-5-(4-buta-1,3-diynylphenyl)-1H-imidazole (3.4) and 2-((S)-1-methyl-pyrrolidin-2-yl)-5-iodo-1H-imidazole (3.5).

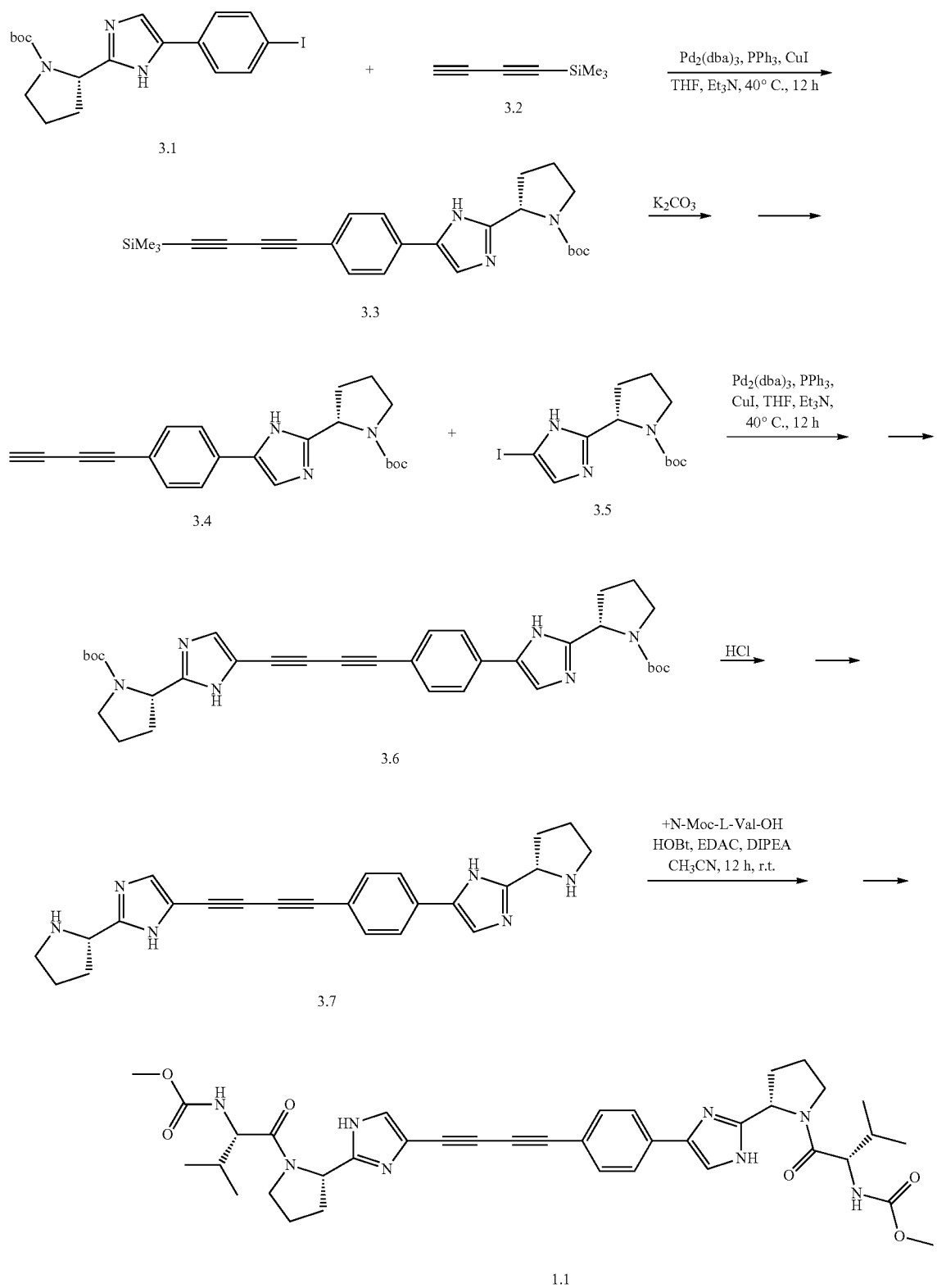

Inhibitors 1.2 and 1.3 were obtained by starting from 2-((S)-1-Boc-pyrrolidin-2-yl)-5[4-(4-trimethylsilanyl-buta-1,3-diynyl)-phenyl]-1H-imidazole (3.3) according to the following scheme. The resulting four-step synthesis {(S)-2-methyl-1-[(S)-2-(5-{4-[4-((S)-2-pyrrolidin-2-yl-3H-imidazol-4-yl)-buta-1,3-diynyl]-phenyl}-1H-imidazol-2-yl)-pyrrolidine-1-carbonyl]-propyl}-carbamic acid methyl ester (3.11) is acylated with N-Moc-(R)-2-phenylglycine or N-Moc-(S)-2-phenylglycine to give inhibitors 1.2 or 1.3.

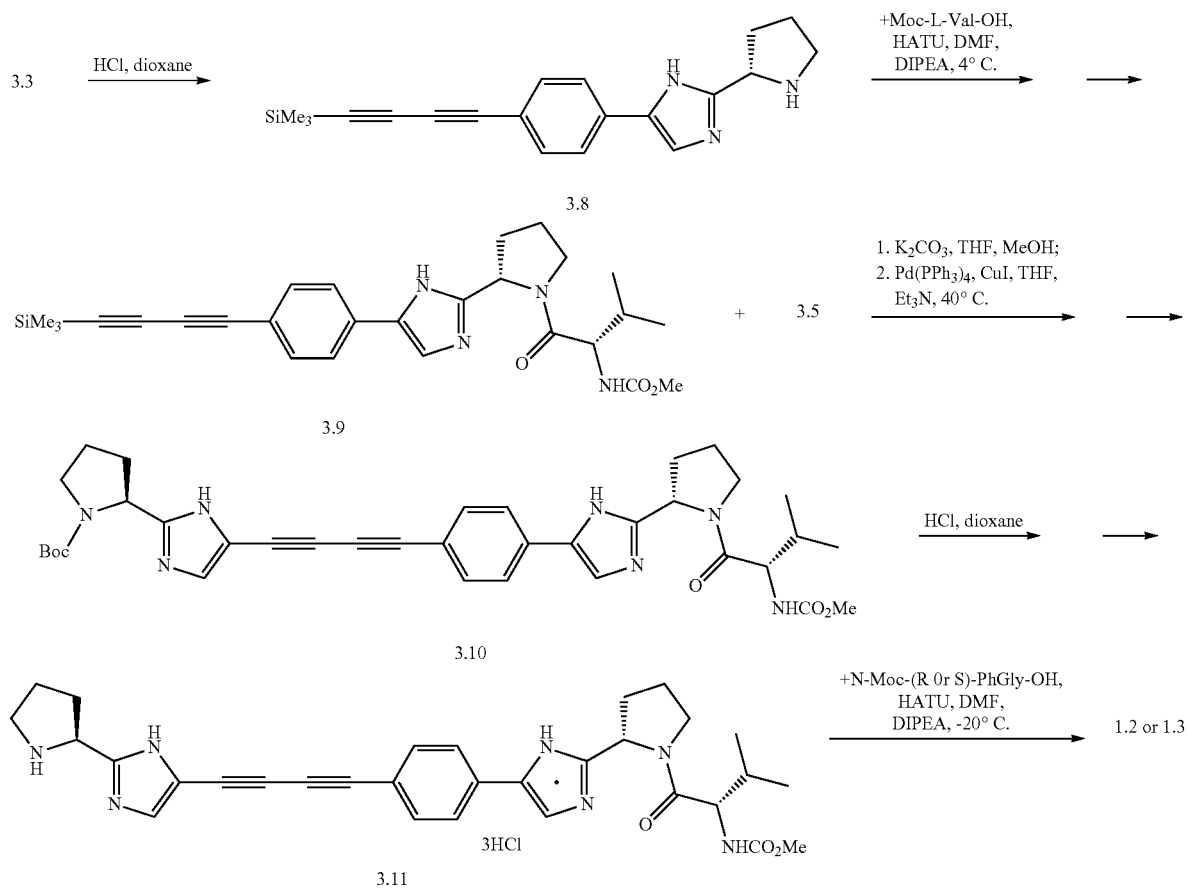
Inhibitors of 1.4 and 1.5 have been prepared according to the following scheme below, by analogy with the above syntheses, but as a key building block was used (S)-2,3-dimethyl-1-[(S)-2-(5-{4-[4-((S)-2-pyrrolidin-2-yl-3H-imidazol-4-yl)-phenyl]-buta-1,3-diynyl}-1H-imidazol-2-yl)-pyrrolidin-1-yl]-butan-1-one (3.14).
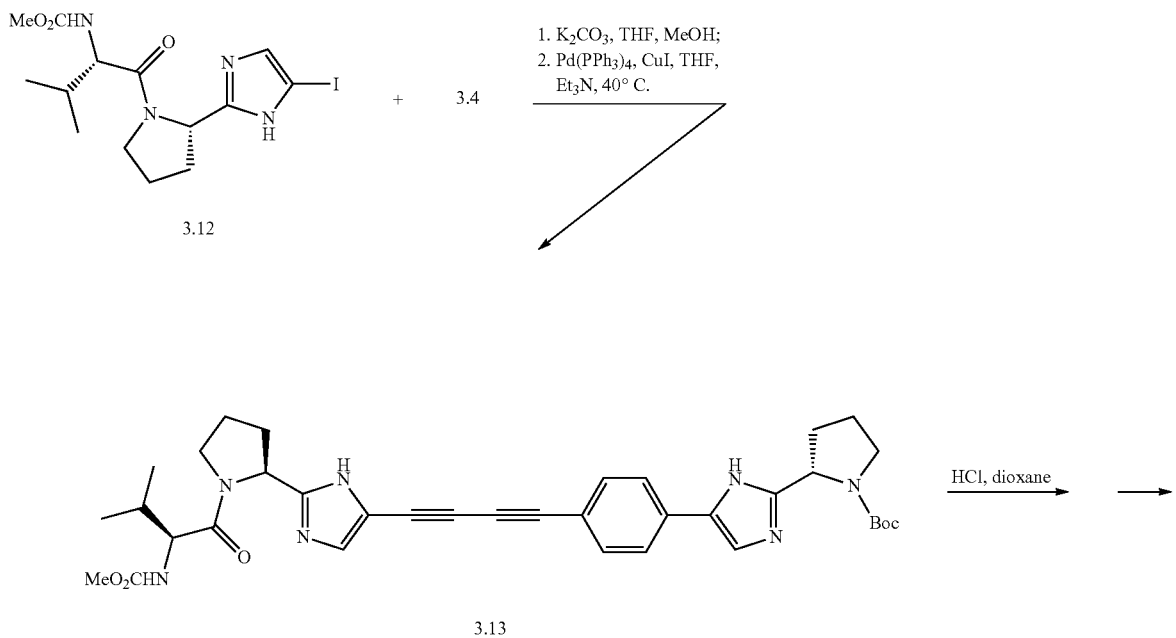

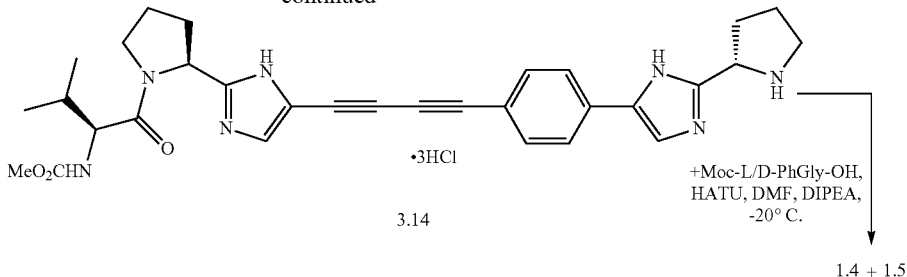

Preparation of NS5A inhibitors 1.6-1.8 which include buta-1,3-diynyl-naphtalene moiety is presented below on the following synthetic scheme. Synthesis of these inhibitors implemented from appropriate bromonaphthalen 3.15-3.17 which in resulting six steps were converted into the corresponding target products 1.6-1.8.

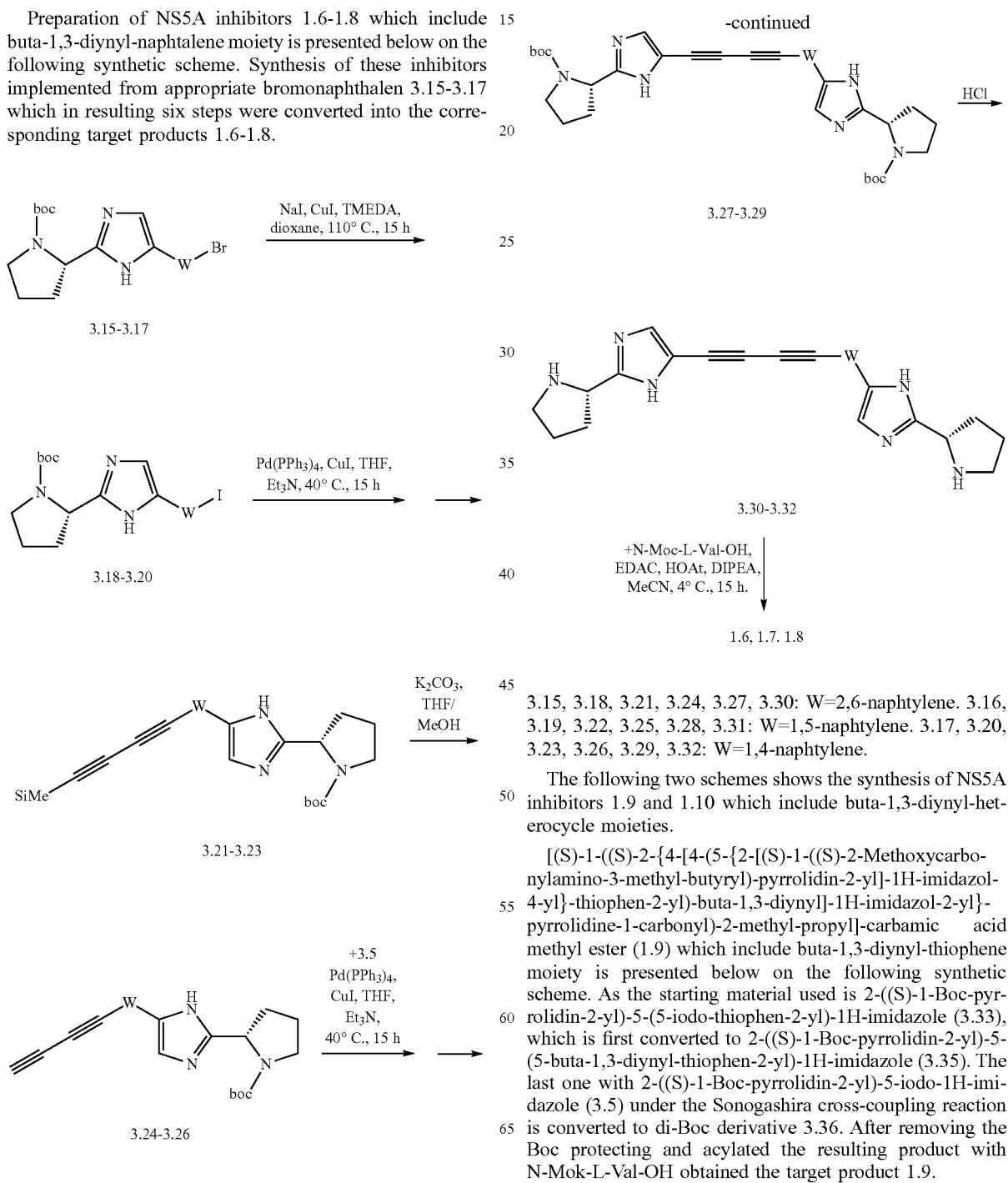

3.15, 3.18, 3.21, 3.24, 3.27, 3.30: W=2,6-naphtylene. 3.16, 3.19, 3.22, 3.25, 3.28, 3.31: W=1,5-naphtylene. 3.17, 3.20, 3.23, 3.26, 3.29, 3.32: W=1,4-naphtylene.

The following two schemes shows the synthesis of NS5A inhibitors 1.9 and 1.10 which include buta-1,3-diynyl-heterocycle moieties.

[(S)-1-((S)-2-{4-[4-(5-{2-[(S)-1-((S)-2-Methoxycarbonylamino-3-methyl-butyryl)-pyrrolidin-2-yl]-1H-imidazol-4-yl}-thiophen-2-yl)-buta-1,3-diynyl]-1H-imidazol-2-yl}-pyrrolidine-1-carbonyl)-2-methyl-propyl]-carbamic acid methyl ester (1.9) which include buta-1,3-diynyl-thiophene moiety is presented below on the following synthetic scheme. As the starting material used is 2-((S)-1-Boc-pyrrolidin-2-yl)-5-(5-iodo-thiophen-2-yl)-1H-imidazole (3.33), which is first converted to 2-((S)-1-Boc-pyrrolidin-2-yl)-5-(5-buta-1,3-diynyl-thiophen-2-yl)-1H-imidazole (3.35). The last one with 2-((S)-1-Boc-pyrrolidin-2-yl)-5-iodo-1H-imidazole (3.5) under the Sonogashira cross-coupling reaction is converted to di-Boc derivative 3.36. After removing the Boc protecting and acylated the resulting product with N-Mok-L-Val-OH obtained the target product 1.9.

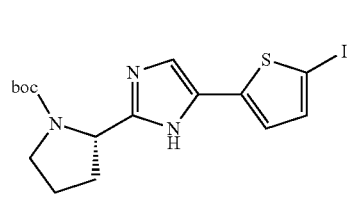 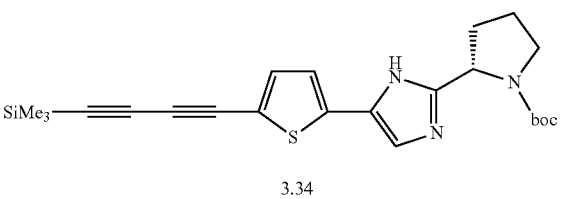

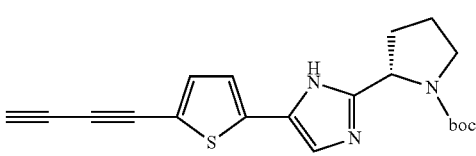

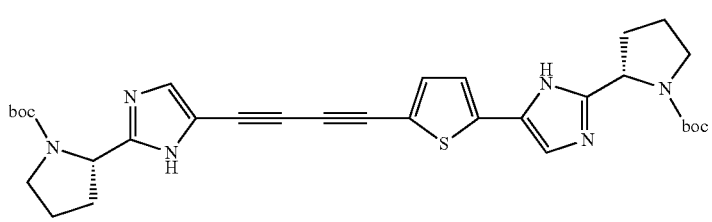

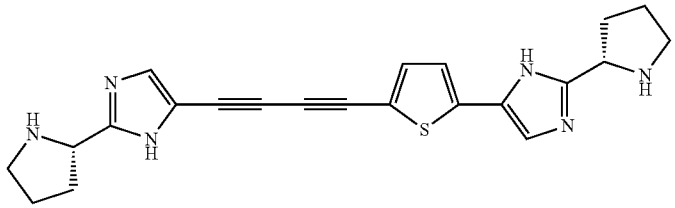

[(S)-1-((S)-2-{5-[6-(4-{2-[(S)-1-((S)-2-Methoxycarbonylamino-3-methyl-butyryl)-pyrrolidin-2-yl]-3H-imidazol-4-yl}-buta-1,3-diynyl)-thieno[3,2-b]thiophen-3-yl]-1H-imidazol-2-yl}-pyrrolidine-1-carbonyl)-2-methyl-propyl]-carbamic acid methyl ester (1.10) which include 3-buta-1,3-diynyl-thieno[3,2-b]thiophene moiety is presented below on the following synthetic scheme. The Suzuki coupling reaction of 2-((S)-1-Boc-pyrrolidin-2-yl)-5-iodo-1-(2-trimethylsilanyl-ethoxymethyl)-1H-imidazol-5-ylboronic acid (3.37) and 3,6-dibromo-thieno[3,2-b]thiophene (3.38) affords a product 3.39 which is converted to the iodide 3.40. The last one with 2-((S)-1-Boc-pyrrolidin-2-yl)-5-buta-1,3-diynyl-1H-imidazole (3.41) under the Sonogashira cross-coupling reaction is converted to di-Boc derivative 3.42. After deprotection and acylated the resulting product 3.43 with N-Mok-L-Val-OH obtained the target product 1.10.

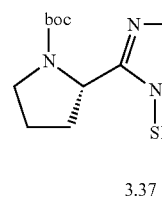 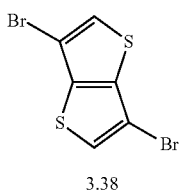

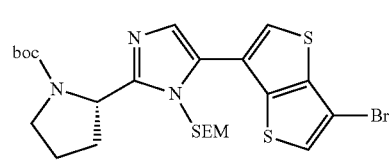 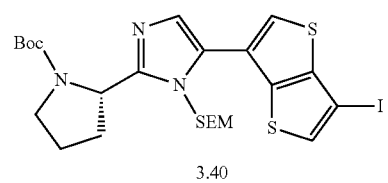

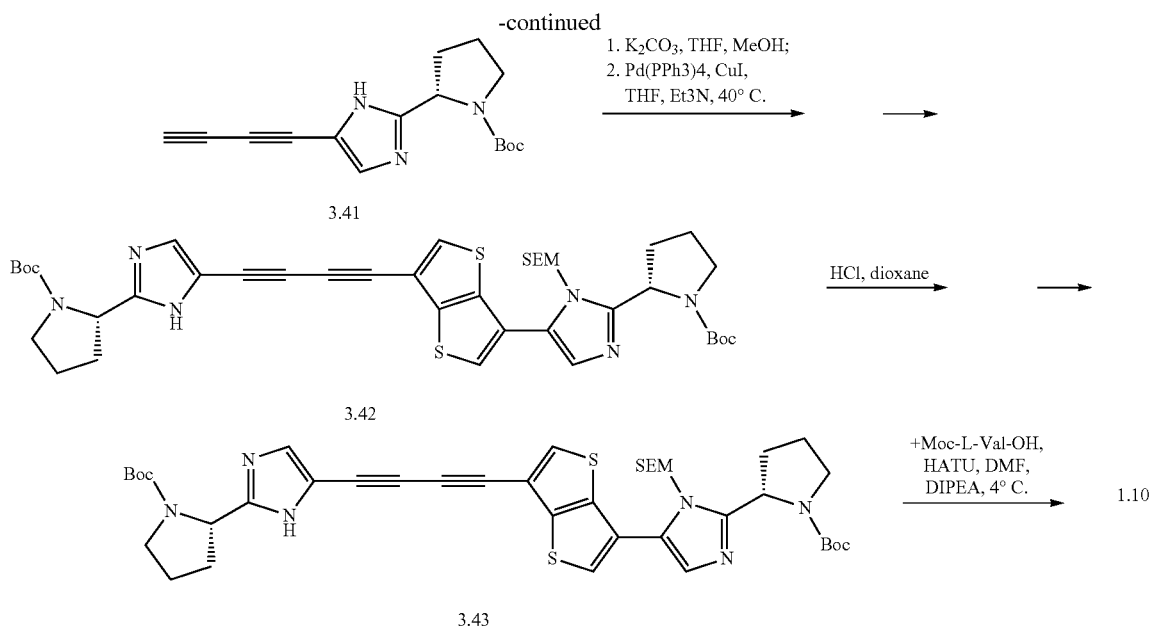

Biological Activity of Azoles of the General Formulas 1

Antiviral activity of substituted azoles of the general formula 1 was determined in the human hepatoma cell line Huh7, comprising subgenomic RNA-replicon HCV (genotype 1b (gT1b), don Con1). A version of immumoenzymatic assay (IEA) on viral protein NS5A in 96-well plate was used as an experimental method. Cytotoxicity of the compounds was estimated in parallel regime. Cells Huh7 were seeded in 96-well plate ($7.5 \times 10^3$ cells to each well in 100 μl of culture medium). Solutions of the tested compounds in DMEM medium {DMEM) 1×; Source: Cellgro; Catalogue: 10-013-CV} were prepared immediately before use. Eleven serial three fold dilutions with variation of concentrations from 20 nM to 0.2 pM were prepared. In 4 hours after seeding, serial dilutions of the compounds were added to the cells (100 μl to each well). Final concentration of tested compounds was varied from 10 nM to 0.1 pM, and DMSO—0.5%. If it was necessary, higher concentrations of the disclosed azoles were investigated. Each dilution of the compound was tested on two identical wells. Then the cells were incubated for three days at 37° C./5% $CO_2$ and fixed by addition of acetone/methanol (1:1) mixture in amount of 250 μl/well. In 1 min the cells were washed 3 times with PBS (Phosphate Buffered Saline) solution. Then the cells were blocked by addition of 10% fetal calf serum in PBS solution in amount of 150 μl/well for 1 h at room temperature. Then, the cells were incubated with mouse monoclonal antibodies to corantigen HCV, don C7-50 (Source: Affinity BioReagents; Catalogue: MA1-080) (100 μl/well, working dilution—1:500 in 10% fetal calf serum in PBS solution) for 2 h at 37° C. The cells were washed 6 times with PBS/0.05% Tween 20 solution, then, they were incubated for 1 h with goat anti-mouse immunoglobulin antibodies (conjugated with horseradish peroxidase, 100 μl/well, working dilution—1:2500 in 10% fetal calf serum in PBS solution). The cells were washed 6 times with PBS/0.05% Tween 20 solution, once with PBS solution, after that substrate (1 tablet of o-phenylenediamine (oPD)+12 ml citrate/phosphate buffer+5 μl 30% $H_2O_2$) in amount of 100 μl/well was added. The plates were kept for 30 min in the dark at room temperature. The reaction was arrested by the addition of 2N $H_2SO_4$ in amount of 100 μl/well, and optical density (wavelength 490 nm) was measured by means of multiscan plate reader Victor3 V 1420 (Perkin Elmer). $IC_{50}$ values (azole concentration, lowering the level of virus RNA-replicon on 50%) for every tested azole were calculated with the help of XLfit 4 program.

Cytotoxicity of the disclosed azoles was tested in experiments in the human hepatoma cell line Huh7. The amount of living cells was determined with the help of ATPLite kit (Perkin Elmer, Boston, USA) in accordance with manufacturer instructions. Cytotoxic action was estimated by seeding the cells into black microplate with transparent bottom (96 wells, $10^4$ cells to each well). Three independent repeatings were used for each bis-azole. The tested bis-azoles were added in 18 h, after that the cells were incubated together with the compounds for 96 h. Each well was washed two times with phosphate buffered saline (0.2 ml/well) and then the cells were lysed by addition of cell buffer (50 μl/well) (all mentioned reagents are included in ATPLite kit). The microplate was incubated for 5 min on a rotating platform at 600 r/min, after that 50 μl of substrate solution (a part of ATPLite kit) was added into each well. The microplate was incubated for additional 5 min on a rotating platform at 600 r/min, kept for 10 min in the dark, after that luminescence was measured using TopCount NXT instrument (Packard, Perkin Elmer).

$CC_{50}$ Value corresponding to bis-azole concentration at which 50% of cells were ruined was used as quantitative characteristic for cytotoxicity estimation. Calculation of $CC_{50}$ value: for calculation of inhibition effectiveness (% Inh) the following equation was used: % Inh=$[(L^{pos}-L^{ex})/L^{pos}-L^{neg})]*100\%$, where $L^{pos}$—positive control, luminescence in the wells with cells without compounds; $L^{neg}$—negative control, luminescence in the wells with medium without cells; $L^{ex}$—luminescence in wells with a compound of definite concentration. Then, $CC_{50}$ values were calculated with the help of XLfit 4 program. Test results for novel azoles of the general formula 1 testify their high (nanomolar) or very high (picomolar) activity. Inhibition activity towards genotype gT1b HCV and $CC_{50}$ of novel azoles of the general formula 1 are shown in the Table.

| No. comp. | $IC_{50}$, nM (gT1b) | $CC_{50}$, nM (gT1b) |
|---|---|---|
| 1.1 | 0.0031 | >10,000.0 |
| 1.1•2HCl | 0.0034 | 85,114.0 |
| 1.1•NDS* | 0.0040 | 19,055.0 |
| 1.2•2HCl | 0.00079 | >10,000.0 |
| 1.3•2HCl | 0.0054 | >10,000.0 |
| 1.4•2HCl | 0.0018 | >10,000.0 |
| 1.5•2HCl | 0.0082 | >10,000.0 |
| 1.6•2HCl | 0.0046 | >10,000.0 |
| 1.7•2HCl | 0.0036 | >10,000.0 |
| 1.8•2HCl | 0.0048 | >10,000.0 |
| 1.9•2HCl | 0.0032 | >10,000.0 |
| 1.10•2HCl | 0.0020 | >10,000.0 |

*naphtalene-1,5-disulfonic acid

The present invention is a novel inhibitor of an nonstructured protein 5A of hepatitis C virus representing substituted 5-{4-[1H-imidazol-5-ylaryl(or hetaryl)]-buta-1,3-diynyl}-1H-imidazole of the general formulas 1 and pharmaceutically acceptable salt thereof.

The present invention is an active component which is a substituted 5-{4-[1H-imidazol-5-ylaryl(or hetaryl)]-buta-1,3-diynyl}-1H-imidazole of the general formulas 1 and pharmaceutically acceptable salt thereof for the pharmaceutical compositions and medicaments for the treatment and prevention of diseases caused by viruses of hepatitis C.

The subject of the present invention is pharmaceutical composition for treatment and prophylaxis of HCV in the form of tablets, capsules, or injections, placed in pharmaceutically acceptable packing comprising an active component which is a substituted 5-4-[1H-imidazol-5-ylaryl(or hetaryl)]-buta-1,3-diynyl}-1H-imidazole of the general formulas 1 and pharmaceutically acceptable salt thereof in pharmaceutically effective amount.

Pharmaceutical compositions may include pharmaceutically acceptable excipients. Pharmaceutically acceptable excipients mean diluents, auxiliary agents and/or carriers applied in the sphere of pharmaceutics. According to the invention pharmaceutical composition in addition to the active component of the general formula 1 may include other active ingredients provided that they do not give rise to undesirable effects, for example, allergic reactions.

If needed, according to the present invention pharmaceutical compositions can be used in clinical practice in various forms prepared by mixing the said compositions with traditional pharmaceutical carries; for example, peroral forms (such as, tablets, gelatinous capsules, pills, solutions or suspensions); forms for injections (such as, solutions or suspensions for injections, or a dry powder for injections which requires only addition of water for injections before utilization); local forms (such as, ointments or solutions).

According to the present invention the carriers used in pharmaceutical compositions represent carriers which are used in the sphere of pharmaceutics for preparation of commonly applied forms including: binding agents, greasing agents, disintegrators, solvents, diluents, stabilizers, suspending agents, colorless agents, taste flavors are used for peroral forms; antiseptic agents, solubilizers, stabilizers are used in the forms for injections; base materials, diluents, greasing agents, antiseptic agents are used in local forms.

The subject of the present invention is also method for the preparation of pharmaceutical compositions, which consists in mixing of at least one active component of the general formula 1 or its pharmaceutically acceptable salt with inert excipient and/or solvent.

The subject of the present invention is also a method for treatment of hepatitis C by introduction of pharmacologically effective amount of substituted 5-{4-[1H-imidazol-5-ylaryl(or hetaryl)]-buta-1,3-diynyl}-1H-imidazole of the general formulas 1 and pharmaceutically acceptable salt thereof or novel pharmaceutical composition.

Clinical doses of pharmaceutical composition comprising as active component azole of the general formula 1 may be corrected depending on: therapeutic efficiency and bio-accessibility of the active ingredients in patients' organism, rate of their exchange and removal from organism, and age, gender, and severity of patient's symptoms. Thus, the daily intake for adults normally being 10~500 mg. Accordingly, the above effective doses are to be taken into consideration while preparing medicament from the pharmaceutical composition of the present invention, each dose unit of the medicament contains 10~500 mg of substituted 5-{4-[1H-imidazol-5-ylaryl(or hetaryl)]-buta-1,3-diynyl}-1H-imidazole of the general formulas 1 and pharmaceutically acceptable salt thereof. Following the instructions of physician or pharmacist, the medicaments may be taken several times over specified periods of time (preferably, from one to six times).

The subject of the present invention is also a therapeutic kit for prophylaxis and treatment of diseases caused by HCV comprising at least one substituted 5-{4-[1H-imidazol-5-ylaryl(or hetaryl)]-buta-1,3-diynyl}-1H-imidazole of the general formulas 1 and pharmaceutically acceptable salt thereof or pharmaceutical composition comprising at least one substituted 5-{4-[1H-imidazol-5-ylaryl(or hetaryl)]-buta-1,3-diynyl}-1H-imidazole of the general formulas 1 and pharmaceutically acceptable salt thereof.

The therapeutic kits for prophylaxis and treatment of HCV, along with the drug substances disclosed in the invention, may include: inhibitors inosine-5-monophosphate dehydrogenase, for example, Ribavirin (allowed) and Ribamidine; inhibitors of NS3 hepatisis C protease, for example, Telaprevir and Boceprevir; inhibitors of RNK-polimeraze NS5B, for example, VX222, R7128, PF-868554, ANA598; alpha-glucosidase inhibitors, for example, aminocarbohydrate Selgozivir; and also TLR-receptor agonists, hepatoprotectors, cyclosporines, various proteins (for example, interferons), antibodies, vaccines etc.

For combination therapies any classes of agents that may be useful when combined with substituted azoles of the present invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, replication or HCV maturation or virus release. Specific compounds in these classes and useful in this invention include, but are not limited to, macrocyclic, heterocyclic and linear HCV protease inhibitors such as telaprevir (VX-950), boceprevir (SCH-503034), narlaprevir (SCH-900518), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor) VX-500, VX-813, PHX-1766, PHX2054, IDX-136, IDX-316, ABT-450 EP-013420 (and congeners) and VBY-376; the Nucleosidic HCV polymerase (replicase) inhibitors useful in the invention include, but are not limited to, R7128, PSI-7851, IDX-184, IDX-102, R1479, UNX- 08189, PSI-6130, PSI-938 and PSI-879 and various other nucleoside and nucleotide analogs and HCV inhibitors including (but not limited to) those derived as 2'-C-methyl modified nucleoside and nucleotide; and 7'-deaza modified nucleoside and nucleotide. Non-nuclosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, NS5A inhibitors of the present invention may be used in combination with cyclophyllin and immunophyllin antagonists (for example, without limitation, DEBIO compounds, NM-811, as well as cyclosporine and its derivatives), kinase inhibitors, inhibitors of heat shock proteins (for example, HSP90, HSP70), other immunomodulatory agents that may include, without limitation, interferons (alpha-, beta-, omega-, gamma-, lambda or synthetic), such as Intron A™, Roferon-A™, Canferon-A300™, Advaferon™, Infergen™, Humoferon™, Sumiferon MP™, Alfaferon™, IFN-β™, Feron™, and the like, polyethylene glycol derivatized (pegylated) interferon compounds, such as: PEG interferon-α-2a (Pegasys™), PEG interferon-α-2b (PEGIntron™), pegylated IFN-α-con 1 and the like; long acting formulations and derivatives of interferon compounds, such as albumin-fused interferon, Albuferon™, Locteron™, and the like; interferons with various types of controlled delivery systems (e.g. ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists, such as: CpG-10101 (action), isotorabine, ANA773 and the like; thymosin α-1, ANA-245 and ANA-246, histamine dihydrochloride, propagermanium; tetrachlorodecaoxide; ampligen; IMP-321; KRN-7000; antibodies, such as: civacir, XTL-6865 and the like and prophylactic and therapeutic vaccines, such as: Inno Vac, HCV EIE2/MF59 and the like. In addition, any of the above-described methods involving administering an NS5A inhibitor, a Type 1 interferon receptor agonist (e.g., an IFN-α) and a Type 2 interferon receptor agonist (e.g., IFN-γ) can be augmented by administration of an effective amount of TNF-α antagonist. Exemplary, non-limiting TNF-α antagonists that are suitable for use in such combination therapies include ENBREL™ and HUMIRA™.

In addition, NS5A inhibitors of the present invention may be used in combination with antiprotozoans and other antivirals thought to be effective in the treatment of HCV infection, such as, the prodrug nitazoxanide. Nitazoxanide can be used as an agent in combination with the compounds disclosed in this invention as well as in combination with other agents useful in treating HCV infection such as peginterferon alfa-2a and ribavarin (see, for example, Rossignol, J F and Keeffe, E B, *Future Microbiol.* 3:539-545, 2008).

NS5A inhibitors of the present invention may also be used in combination with alternative forms of interferons and pegylated interferons, ribavirin or its analogs (e.g., Tarabavarin, levovirion), microRNA, small interfering RNA compounds (e.g., SIRPLEX-140-N) and the like, nucleotide or nucleoside analogs, immonoglobulins, hepatoprotectants, anti-inflammatory agents and other inhibitors of NS5A. Inhibitors of other targets in the HCV life cycle include NS3 helicase inhibitors; NS4A co-factor inhibitors, antisense oligonucleotide inhibitors, such as ISIS-14803, AVI-4065 and the like; vector-encoded short hairpin RNA (shRNA); HCV specific ribozymes such as heptazyme, RPI, 139199 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative compounds HCV inhibitor compounds include those disclosed in the known scientific and patent publications.

Additionally, combinations of, for example, ribavirin and interferon may be administered as multiple combination therapy with at least one azole of the present invention. The present invention is not limited to the aforementioned classes or compounds and contemplates known and new compounds and combinations of biologically active agents. It is intended that combination therapies of the present invention include any chemically compatible combination of an bis-azole of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the present invention or where one treatment comprises a compound of the present invention and the other comprises one or more biologically active agents) or it can be treatment with both agents at the same time. Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. For any particular subject specific dosage regimens and schedules may be adjusted over time according to the individual's need and the professional judgement of the person administering or supervising the administration of the combination therapy.

Although the foregoing invention has been described in some detail by way of illustration and example for purposes of clarity of understanding, it will be readily apparent to one of ordinary skill in the art in light of the teaching of this invention that certain changes and modifications may be made thereto without departing from the spirit or scope of the invention as defined in the appended claims.

BEST EMBODIMENT OF THE INVENTION

Below the invention is described by means of specific examples, which illustrate but not limit the scope of the invention.

Example 1

[(1S)-1-[[(2S)-2-[5-[4-[4-[2-[(2S)-1-[(2S)-2-[(Methoxycarbonyl)amino]-3-methyl-1-oxobutyl]-2-pyrrolidinyl]-1H-imidazol-5-yl]-1,3-butadiynyl]phenyl]-1H-imidazol-2-yl]-1-pyrrolidinyl]carbonyl]-2-methylpropyl]-carbamic acid methyl ester dihydrochloride 1.1•2HCl 1.1

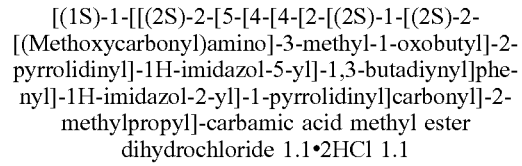

1.5 M MeLi×LiBr solution in ether (31 ml, 46.5 mmol) was added to solution of 1,4-bis-trimethylsilyl)-1,3-butadiyne (8.15 g, 42 mmol) in dry ether (50 ml) under argon. The mixture was stirred at room temperature for 6 ч. Then, saturated NH$_4$Cl solution (50 ml) was slowly added to the mixture, extracted with pentane, dried over Na$_2$SO$_4$ and the solvents were evaporated in soft vacuo. Liquid residue 3.2 was dissolved in THF (70 ml), then triethylamine (20 ml), compound 3.1 (8.8 g, 20 mmol), Pd$_2$(dba)$_3$ (458 mg, 0.5 mmol), triphenyl phosphine (524 mg, 2 mmol), CuI 190 mg (1 mmol) were added one after another and the resultant mixture was stirred for 12 h at 40° C. under argon. The mixture was filtered through celit, applied to silica gel and compound 3.3 was isolated by flash-chromatography (eluent CHCl$_3$: EtOAc=10:1). Yield is 7.56 g (87%). LCMS (M+H)$^+$ 434. K$_2$CO$_3$ (7.04 g, 51 mmol) was added to solution of compound 3.3 (7.36 g, 17 mmol) in THF (120 ml) and methnol (120 ml) and the resultant mixture was stirred for 2 h. The solvents were evaporated in vacuo, the residue was treated with THF (150 ml) and filtered. 2-[(2S)-1-Boc-pyrrolidin-2-yl]-5-iodo-1H-imidazol 3.5 (5.56 g, 15.3 mmol), Pd$_2$(dba)$_3$ (366 mg, 0.4 mmol), triphenyl phosphine (630 mg, 2.4 mmol), and CuI (152 mg, 0.8 mmol) were subsequently added to the obtained solution of compound 3.4, and the resultant mixture was stirred for 12 h at 40° C. under argon. Then, the reaction mixture was filtered through celit, applied to silica gel and compound 3.6 was separated from the main part of admixtures by flash-chromatography (eluent CHCl$_3$:MeOH=80:1). After evaporation of the solvent the residue was treated with acetonitrile (60 ml), kept in ultrasound-bath till the beginning of crystallisation and left for 3 h. The precipitated solid was filtered off, washed with acetonitrile, ether and dried in vacuo. Yield is 5.47 r (54%). LCMS (M+H)$^+$ 597. 3M HCl solution in dioxane (15 ml) was added to compound 3.6 (0.695 g) and stirred for 12 h. After that the mixture was evaporated in vacuo, it gave compound 3.7, yield is 55%. LCMS (ESI): LCMS (M+H)$^+$ 397. $^1$H NMR (DMSO-d$_6$, 400 MHz) δ 2.02 (br.s., 8H), 2.99 (m, 4H), 3.40 (br.s., 2H), 6.22 (m, 4H), 6.75 (s, 1H), 7.22 (s, 1H), 7.77 (m, 2H), 7.83 (d, 2H). Mixture of N-methoxycarbonyl-L-valine (50 mg, 0.283 mmol, 2.4 eq.), 1-hydroxybenzotriazole (40 mg, 0.295 mmol, 2.5 eq.) and N-(3-dimethylaminopropyl)-N'-ethylcarbodiimide hydrochloride (53 mg, 0.277 mmol, 2.35 eq.) in acetonitrile (1 ml) was stirred for 1 h, then compound 3.7 (64 mg, 0.118 mmol, 1 eq.) and 82 mid (61 mg, 0.472 mmol, 4 eq.) diisopropylamine were added. The reaction mixture was stirred for 12 h at room temperature. Completeness of the reaction was controlled by LCMS method. After the reaction was completed the solvent was evaporated to dryness on rotary evaporator, the residue was dissolved in dichloromethane. Extract was washed with 10% Na$_2$CO$_3$ solution, dried over Na$_2$SO$_4$ and evaporated on rotary evaporator. Further purification of 1.1 was carried out by HPLC method. Dihydrochloride 1.1•2HCl was prepared by addition of excess of 3M HCl solution in dioxane to a solution of 1.1 base in CH$_2$Cl$_2$ and precipitation with ether. It gave 56 mg (67%) of compound 1.1•2HCl. LCMS (M+1)$^+$ 711. $^1$H NMR (DMSO-d$_6$, 400 MHz) δ 0.87 (t, J$_1$=6.50, J$_2$=0.93, 6H), 0.97 (t, J$_1$=6.50, J$_2$=0.93, 6H), 1.64 (m, 2H), 1.84 (m, 2H), 1.99 (m, 4H), 2.06 (m, 2H), 3.56 (m, 2H), 3.63 (m, 8H), 4.02 (d, J=0.42, 2H), 4.73 (m, 2H), 6.86 (s, 1H), 7.33 (s, 1H), 7.76 (d, J=8.26, 2H), 7.90 (m, 2H), 8.80 (m, 4H).

Example 2

Methyl (R)-(1.2•2HCl) and methyl (S)-[(S)-2-(5-{4-[4-(2-{(S)-1-[(S)-2-(methoxycarbonylamino)-3-methylbutanoyl]pyrrolidin-2-yl}-3H-imidazol-4-yl) buta-1,3-diynyl]phenyl}-1H-imidazol-2-yl) pyrrolidin-1-yl]-2-oxo-1-phenylethylcarbamate dihydrochloride (1.3•2HCl)

Hydrochloric acid (HCl) in dioxane (4 M, 25 mL) was added to the solution of compound 3.3 (4.34 g, 10 mmol) in dioxane (25 mL). The resulting mixture was then stirred for 4 h, rotovapped, washed with ether and dried under vacuum to obtain 4.02 g (99%) of (S)-2-(pyrrolidin-2-yl)-5-{4-[(trimethylsilyl)buta-1,3-diynyl]phenyl}-1H-imidazole dihydrochloride (3.8). The LC-MS molecular ion peak was at 334 (M+H)$^+$. $^1$H NMR (DMSO-d$_6$, 400 MHz) δ 10.35 (br s, 1H), 9.74 (br s, 1H), 8.12 (m, 1H), 7.95 (m, 2H), 7.67 (d, J=8.0 Hz, 2H), 4.98 (m, 1H), 3.43 (m, 1H), 3.36 (m, 1H), 2.44 (m, 2H), 2.18 (m, 1H), 2.00 (m, 1H), 0.22 (s, 9H). The mixture of compound 3.8 (406 mg, 1 mmol), N-Moc-L-valine (184 mg, 1.05 mmol) and HATU (418 mg, 1.1 mmol) in DMF (4 mL) was stirred in a fridge for 0.5 h, then DIPEA (517 mg, 4 mmol, 0.697 mL) was added, and the resulting mixture was continuously stirred in a fridge for 2 h. The mixture was diluted with 20 mL of benzene, washed twice with a 5% Na$_2$CO$_3$ solution, dried over Na$_2$SO$_4$, rotovapped and subjected to dry flash chromatography on silica gel (EtOAc) to obtain 314 mg (64%) of methyl (S)-3-methyl-1-oxo-1-[(S)-2-(5-{4-[(trimethylsilyl)buta-1,3-diynyl]phenyl}-1H-imidazol-2-yl)pyrrolidin-1-yl]butan-2-ylcarbamate (3.9). The LC-MS molecular ion peak was at 491 (M+H)$^+$. Potassium carbonate (K$_2$CO$_3$) (265 mg, 1.92 mmol) was added to the solution of compound 3.9 (314 mg, 0.64 mmol) in THF (10 mL) and methanol (10 mL), and the reaction mixture was stirred under an argon atmosphere (aa) for 2 h, then filtered and rotovapped. Triethylamine (2 mL), tert-butyl (S)-2-(5-iodo-1H-imidazol-2-yl)-pyrrolidine-1-carboxylate (3.5) (232 mg, 0.64 mmol), Pd(PPh)$_4$ (37 mg, 0.032 mmol) and CuI (12 mg, 0.064 mmol) were added to the solution of the obtained compound 5 in THF (8 mL). The resulting mixture was then stirred under aa at 40° C. for 15 h. After the reaction was completed, the mixture was rotovapped, dissolved in DCM, filtered, washed with a sat. NH$_4$Cl solution, rotovapped again and subjected to column chromatography on silica gel (gradient toluene/dioxane from 5:1 to 3:2) to obtain 276 mg (66%) of (S)-tert-butyl 2-(5-{[4-(2-{(S)-1-[(S)-2-(methoxycarbonylamino)-3-methylbutanoyl]pyrrolidin-2-yl}-1H-imidazol-5-yl)phenyl] buta-1,3-diynyl}-1H-imidazol-2-yl)pyrrolidine-1-carboxylate (3.10). The LC-MS molecular ion peak was at 654 (M+H)$^+$. Compound 3.10 was treated according to the procedure given above for compound 3.8 to obtain methyl (S)-3-methyl-1-oxo-1-{(S)-2-[5-(4-{[2-((S)-pyrrolidin-2-yl)-1H-imidazol-5-yl]buta-1,3-diynyl}phenyl)-1H-imidazol-2-yl]pyrrolidin-1-yl}butan-2-ylcarbamate trihydrochloride (3.11). Yield 257 mg (92%). The LC-MS molecular ion peak was at 554 (M+H)$^+$. The mixture of compound 3.11 (133 mg, 0.2 mmol) and N-Moc-(R)-2-phenylglycine[2] (44 mg, 0.21 mmol) in DMF (4 mL) was cooled to −10° C. and HATU (84 mg, 0.22 mmol) was added. After dissolution the mixture was left in a freezer for 0.5 h, then DIPEA (129 mg, 1 mmol, 0.174 mL) was added, and the resulting mixture was left in a freezer for 3 h. After the reaction completed (LC-MS check) the mixture was diluted with 20 mL of benzene, washed twice with a 5% Na$_2$CO$_3$ solution, dried over Na$_2$SO$_4$, rotovapped and subjected to HPLC to obtain 70 mg (47%) of methyl (R)-[(S)-2-(5-{4-[4-(2-{(S)-1-[(S)-2-(methoxycarbonylamino)-3-methylbutanoyl]pyrrolidin-2-yl}-3H-imidazol-4-yl)buta-1,3-diynyl]phenyl}-1H-imidazol-2-yl)pyrrolidin-1-yl]-2-oxo-1-phenylethylcarbamate (1.2). It was dissolved in acetone (2 mL), treated with 10% excess of 4M HCl solution in ethyl acetate and with ether (6 mL), the precipitate was centrifuged off and dried in vacuum to obtain 72 mg (94%) of methyl (R)-[(S)-2-(5-{4-[4-(2-{(S)-1-[(S)-2-(methoxycarbonylamino)-3-methylbutanoyl]pyrrolidin-2-yl}-3H-imidazol-4-yl)buta-1,3-diynyl]phenyl}-1H-imidazol-2-yl)pyrrolidin-1-yl]-2-oxo-1-phenylethylcarbamate dihydrochloride (1.2•2HCl). The LC-MS molecular ion peak was at 745 (M+H)+.

Methyl (5)-[(S)-2-(5-{4-[4-(2-{(S)-1-[(S)-2-(methoxycarbonylamino)-3-methylbutanoyl]pyrrolidin-2-yl}-3H-imidazol-4-yl)buta-1,3-diynyl]phenyl}-1H-imidazol-2-yl)pyrrolidin-1-yl]-2-oxo-1-phenylethylcarbamate dihydrochloride (1.3•2HCl). The later procedure with N-Moc-(S)-2-phenylglycine[2] afforded 1.3•2HCl with 45% yield. The LC-MS molecular ion peak was at 745 (M+H)+.

Example 3

Methyl (R)-(1.4•2HCl) and methyl (S)-[(S)-2-(5-{4-[4-(2-{(S)-1-[(S)-2-(methoxycarbonylamino)-3-methylbutanoyl]pyrrolidin-2-yl}-3H-imidazol-4-yl)buta-1,3-diynyl]phenyl}-1H-imidazol-2-yl)pyrrolidin-1-yl]-2-oxo-1-phenylethylcarbamate dihydrochloride (1.5•2HCl)

Compounds 1.4 and 1.5 were synthesized from 3.12 and 3.4 by the same procedures given for synthesis of 1.2 and 1.3 (Example 2). (S)-tert-Butyl 2-(5-{4-[(2-{(S)-1-[(S)-2-(methoxycarbonylamino)-3-methylbutanoyl]pyrrolidin-2-yl}-1H-imidazol-5-yl)buta-1,3-diynyl]phenyl}-1H-imidazol-2-yl)pyrrolidine-1-carboxylate (3.13). Yield 60%. The LC-MS molecular ion peak was at 654 (M+H)+. Methyl (S)-3-methyl-1-oxo-1-{(S)-2-[5-({4-[2-((S)-pyrrolidin-2-yl)-1H-imidazol-5-yl]phenyl}buta-1,3-diynyl)-1H-imidazol-2-yl]pyrrolidin-1-yl}butan-2-ylcarbamate trihydrochloride (3.14). Yield 78%. The LC-MS molecular ion peak was at 554 (M+H)+. Methyl (R)-[(S)-2-(5-{4-[4-(2-{(S)-1-[(S)-2-(methoxycarbonylamino)-3-methylbutanoyl]pyrrolidin-2-yl}-3H-imidazol-4-yl)buta-1,3-diynyl]phenyl}-1H-imidazol-2-yl)pyrrolidin-1-yl]-2-oxo-1-phenylethylcarbamate dihydrochloride (1.4•2HCl). Yield 40%. The LC-MS molecular ion peak was at 745 (M+H)+. Methyl (S)-[(S)-2-(5-{4-[4-(2-{(S)-1-[(S)-2-(methoxycarbonylamino)-3-methylbutanoyl]pyrrolidin-2-yl}-3H-imidazol-4-yl)buta-1,3-diynyl]phenyl}-1H-imidazol-2-yl)pyrrolidin-1-yl]-2-oxo-1-phenylethylcarbamate dihydrochloride (1.5•2HCl). Yield 44%. The LC-MS molecular ion peak was at 745 (M+H)+.

Example 4

General Procedure for Preparation of Inhibitors 1.6•HCl, 1.7•HCl, 1.8•HCl

A mixture of 884 mg (2 mmol) of tert-butyl (S)-2-[5-(bromonaphthalenyl)-1H-imidazol-2-yl]-pyrrolidine-1-carboxylate (3.15-3.17), 494 mg (4 mmol) of NaI, 38 mg (0.2 mmol) of CuI and 36 mg (0.4 mmol) of N,N,N',N'-tetramethylethylenediamine in 4 mL of dioxane was stirred in a capped tube under argon at 110° C. for 15 h. After cooling down the mixture was diluted with DCM, washed with water, dried over $Na_2SO_4$ and rotavaped. The residue was purified by dry flash chromatography on $SiO_2$, eluent $CHCl_3$: $Me_2CO$=20:1 and obtain (86-92%) of tert-butyl (S)-2-[5-(iodonaphthalenyl)-1H-imidazol-2-yl]-pyrrolidine-1-carboxylates 3.18-3.20. LC-MS (ESI) 491 (M+H)+. To a stirred solution of 5.83 g (30 mmol) of 1,4-bis(trimethylsilyl)buta-1,3-diyne in 40 mL of ether under argon was added 21 mL (31.5 mmol) of 1.5 M methyllithium lithium bromide complex solution in ether. The mixture was stirred at room temperature for 15 h, then cooled in ice bath and quenched with 40 mL of saturated $NH_4Cl$ solution. The organic layer was washed with brine, dried over $Na_2SO_4$ and the solvent was stripped off on rotovap in a week vacuum. To a solution of the residual liquid in 70 mL of THF was added 20 mmol iodide 3.18-3.20, 20 mL of TEA, 1.16 g (1 mmol) of $Pd(PPh)_4$, 0.19 g (1 mmol) of CuI and the mixture was stirred under argon at 40° C. for 15 h. The mixture was filtered through a celite, rotavaped and subjected to column chromatography on $SiO_2$ (eluent chloroform:acetone=15:1) to afford (85%) of 3.21-3.23. LC-MS (ESI) 484 (M+H)+. To a solution of 17 mmol of compound 3.21-3.23 in 120 mL of THF and 120 mL of methanol was added 7.04 g (51 mmol) of $K_2CO_3$ and the mixture was stirred under argon for 2 h, then filtered and rotavaped. Obtained buta-1,3-diynyl derivatives 3.24-3.26. To a solution of the obtained compound 3.24-3.26 in 60 mL of THF was added 6.17 g (17 mmol) of tert-butyl (S)-2-(5-iodo-1H-imidazol-2-yl)-pyrrolidine-1-carboxylate (3.5), 20 mL of TEA, 0.93 g (0.8 mmol) of $Pd(PPh)_4$, 0.15 g (0.8 mmol) of CuI and the mixture was stirred under argon at 40° C. for 15 h. The mixture was filtered, the precipitate washed with chloroform—methanol 3:1 solution, the filtrare was rotavaped and the residue was boiled up in 100 mL of methanol. The cooled mixture was stirred in a fridge for 4 h, the precipitate of 3.27-3.29 was filtered off, washed with cold methanol, then with ether and dried. Yield 55-65%, LC-MS (ESI) 647 (M+H)+. To 5.78 g (9.7 mmol) of compound 3.27-3.29 was added 25 mL of 4 M HCl solution in dioxane and the mixture was stirred for 15 h. The precipitate was filtered off, washed with ether and dried in vacuum to obtain (96-99%) of 2-(S)-pyrrolidin-2-yl-5-{[4-((S)-2-pyrrolidin-2-yl-3H-imidazol-4-yl)-buta-1,3-diynyl]-naphthalenyl}-1H-imidazole tetrahydrochloride (3.30-3.32). LC-MS (ESI) 446 (M+H)+. A mixture of 50 mg (0.283 mmol) of N-Moc-L-valine, 40 mg (0.295 mmol) of 1-hydroxy-7-azabenzotriazole (HOAt) and 53 mg (0.277 mmol) of EDAC in 1 mL of acetonitrile was stirred in a fridge for 1 h, then 64 mg (0.118 mmol) of compound 3.30-3.32 and 82 μL (61 mg, 0.472 mmol) of DIPEA were added and the mixture was stirred in a fridge for 15 h. The mixture was rotavaped, dissolved in dichloromethane, washed twice with 5% $Na_2CO_3$ solution, dried over $Na_2SO_4$, rotavaped and subjected to HPLC. Inhibitor 1.6-1.8 was obtained by addition of excess of 4 M HCl solution in dioxane to a solution of the base in acetone. Yield dihydrochloride of 1.6-1.8 is 67-75%. LC-MS (ESI) 761 (M+H)+. Methyl [(S)-1-((S)-2-{5-[2-(4-{2-[(S)-1-((S)-2-methoxycarbonylamino-3-methyl-butyryl)-pyrrolidin-2-yl]-3H-imidazol-4-yl}-buta-1,3-diynyl)-naphthalen-6-yl]-1H-imidazol-2-yl}-pyrrolidine-1-carbonyl)-2-methyl-propyl]-carbamate dihydrochloride (1.6), $^1$H NMR (DMSO-$d_6$, 400 MHz) δ 15.27 (brs, 0.8H), 14.74 (brs, 0.8H), 8.50 (s, 1H), 8.32 (s, 1H), 8.24 (s, 1H), 8.06 (m, 2H), 7.96 (m, 1H), 7.82 (brs, 0.9H), 7.69 (m, 1H), 7.28 (m, 1.7H), 7.07 (m, 0.07H), 6.85 (brm, 0.08H), 5.71 (m, 0.06H), 5.34 (m, 0.1H), 5.20 (m, 0.94H), 5.04 (m, 0.9H), 4.14 (t, J=8.0 Hz, 1H), 4.06 (t, J=8.0 Hz, 1H), 3.98 (m, 1H), 3.86 (m, 1H), 3.80 (m, 2H), 3.54, 3.55 (2s, 5.55H), 3.45 (s, 0.1H), 3.43 (s, 0.1H), 3.30 (s, 0.25H), 2.40 (m, 1H), 2.20 (m, 3H), 2.13 (m, 1H), 2.08 (m, 1H), 1.99 (m, 4H), 0.91 (m, 1H), 0.81 (m, 11H). Methyl

[(S)-1-((S)-2-{5-[5-(4-{2-[(S)-1-((S)-2-methoxycarbonylamino-3-methyl-butyryl)-pyrrolidin-2-yl]-3H-imidazol-4-yl}-buta-1,3-diynyl)-naphthalen-1-yl]-1H-imidazol-2-yl}-pyrrolidine-1-carbonyl)-2-methyl-propyl]-carbamate dihydrochloride (1.7), $^1$H NMR (DMSO-d$_6$, 400 MHz) δ 14.90 (brs, 1.8H), 8.40 (d, J=8.4 Hz, 1H), 8.28 (d, J=8.4 Hz, 0.11H), 8.03 (m, 2H), 7.96, 7.97 (2s, 1H), 7.85 (m, 2.1H), 7.77 (m, 0.9H), 7.65 (m, 1H), 7.39 (d, J=8.4 Hz, 0.13H), 7.32 (d, J=8.4 Hz, 0.8H), 7.27 (d, J=8.4 Hz, 0.8H), 7.06 (brm, 0.06H), 6.88 (brm, 0.07H), 5.72 (m, 0.1H), 5.35 (m, 0.1H), 5.21 (m, 0.9H), 5.06 (m, 0.9H), 4.14 (t, J=8.0 Hz, 1H), 4.07 (t, J=8.0 Hz, 1H), 3.88 (m, 2H), 3.81 (m, 2H), 3.54, 3.55 (2s, 5.4H), 3.45 (s, 0.1H), 3.43 (s, 0.1H), 3.36 (s, 0.4H), 2.42 (m, 1H), 2.19 (m, 4H), 2.01 (m, 5H), 0.92 (m, 1H), 0.83 (m, 11H). Methyl [(S)-1-((S)-2-{5-[4-(4-{2-[(S)-1-((S)-2-methoxycarbonylamino-3-methyl-butyryl)-pyrrolidin-2-yl]-3H-imidazol-4-yl}-buta-1,3-diynyl)-naphthalen-1-yl]-1H-imidazol-2-yl}-pyrrolidine-1-carbonyl)-2-methyl-propyl]-carbamate dihydrochloride (1.8), $^1$H NMR (DMSO-d$_6$, 400 MHz) δ 14.92 (brs, 1.6H), 8.36 (m, 1.03H), 8.28 (m, 0.13H), 8.04 (m, 2.9H), 7.82 (m, 2.1H), 7.72 (m, 1.8H), 7.32 (m, 1.7H), 7.06 (m, 0.07H), 6.88 (brm, 0.08H), 5.71 (m, 0.1H), 5.34 (m, 0.1H), 5.21 (m, 0.9H), 5.05 (m, 0.9H), 4.14 (t, J=8.0 Hz, 1H), 4.07 (t, J=8.0 Hz, 1H), 3.88 (m, 2H), 3.81 (m, 2H), 3.54, 3.55 (2s, 5.4H), 3.45 (s, 0.1H), 3.43 (s, 0.1H), 3.35 (s, 0.4H), 2.42 (m, 1H), 2.19 (m, 4H), 2.01 (m, 5H), 0.92 (m, 1H), 0.87 (m, 3.1H), 0.82 (m, 7.9H).

Example 5

[(S)-1-((S)-2-{4-[4-(5-{2-[(S)-1-((S)-2-Methoxycarbonylamino-3-methyl-butyryl)-pyrrolidin-2-yl]-1H-imidazol-4-yl}-thiophen-2-yl)-buta-1,3-diynyl]-1H-imidazol-2-yl}-pyrrolidine-1-carbonyl)-2-methyl-propyl]-carbamic acid methyl ester dihydrochloride (1.9•2HCl)

(LC-MS (ESI) 717 (M+H)) was obtained starting from 2-((S)-1-Boc-pyrrolidin-2-yl)-5-(5-iodo-thiophen-2-yl)-1H-imidazole (3.33) in analogy with example 4.

Example 6

Methyl [(S)-1-((S)-2-{5-[6-(4-{2-[(S)-1-((S)-2-Methoxycarbonylamino-3-methyl-butyryl)-pyrrolidin-2-yl]-3H-imidazol-4-yl}-buta-1,3-diynyl)-thieno[3,2-b]thiophen-3-yl]-1H-imidazol-2-yl}-pyrrolidine-1-carbonyl)-2-methyl-propyl]-carbamate dihydrochloride (1.10)

A mixture of 0.715 mmol, (S)-2-[1-(tert-butoxycarbonyl)pyrrolidin-2-yl]-1-[2-(trimethylsilyl)ethoxymethyl]-1H-imidazol-5-ylboronic acid (3.37), 3,6-dibromothieno[3,2-b]thiophene (3.38) (213 mg, (294 mg, 0.715 mmol), Na$_2$CO$_3$ (303 mg, 2.86 mmol) and Pd(PPh$_3$)$_4$ (83 mg, 0.072 mmol) in DMF (10 mL) and water (1 mL) was stirred under aa at 85° C. for 48 h. After the reaction was completed, the mixture was diluted with water, extracted with DCM, washed with water, dried over Na$_2$SO$_4$, rotovapped and subjected to HPLC to obtain 74 mg (18%) of (2S)-tert-butyl 2-(5-(6-bromothieno[3,2-b]thiophen-3-yl)-1-{[2-(trimethylsilyl)ethoxy]methyl}-1H-imidazol-2-yl)pyrrolidine-1-carboxylate (3.39). The LC-MS molecular ion peaks were at 584, 586 (M+H)$^+$. A mixture of compound 3.39 (74 mg, 0.13 mmol), dry sodium iodide (NaI) (95 mg, 0.63 mmol), CuI (8 mg, 0.042 mmol) and N,N'-dimethylethelenediamine (7.5 mg, 0.085 mmol, 9.1 μL) in dioxane (1.5 mL) was stirred under aa at 110° C. for 5 days. After the reaction was completed, the mixture was diluted with water, extracted with DCM, washed with water, dried over Na$_2$SO$_4$, rotovapped and subjected to column chromatography on silica gel (chloroform/acetone 20:1) to obtain 28 mg (35%) of (2S)-tert-butyl 2-(5-(6-iodothieno[3,2-b]thiophen-3-yl)-1-{[2-(trimethylsilyl)ethoxy]methyl}-1H-imidazol-2-yl)pyrrolidine-1-carboxylate (3.40). The LC-MS molecular ion peak was at 632 (M+H)$^+$. Potassium carbonate (K$_2$CO$_3$) (35 mg, 0.25 mmol) was added to the solution of compound 3.41 (30 mg, 0.084 mmol) in THF (3 mL) and methanol (3 mL), and the reaction mixture was stirred under an argon atmosphere for 2 h, then filtered and rotovapped. Triethylamine (0.8 mL), compound 3.40 (28 mg, 0.044 mmol), Pd(PPh)$_4$ (9 mg, 0.008 mmol) and CuI (3 mg, 0.016 mmol) were added to the solution of the obtained compound in THF (3.2 mL). The resulting mixture was then stirred under aa at 40° C. for 15 h. After the reaction was completed, the mixture was rotovapped, dissolved in DCM, filtered, washed with a sat. NH$_4$Cl solution, rotovapped again and subjected to column chromatography on silica gel (hexane/EtOAc 1:1) to obtain 29 mg (83%) of (S)-tert-butyl 2-{5-[(6-{2-[(S)-1-(tert-butoxycarbonyl)pyrrolidin-2-yl]-1-[2-(trimethylsilyl)ethoxymethyl]-1H-imidazol-5-yl}thieno[3,2-b]thiophen-3-yl)buta-1,3-diynyl]-1H-imidazol-2-yl}pyrrolidine-1-carboxylate (3.42). The LC-MS molecular ion peak was at 789 (M+H)$^+$. Hydrochloric acid (HCl) in dioxane (4 M, 1.5 mL) was added to the solution of compound 3.42 (29 mg, 0.037 mmol) in dioxane (1 mL) and methanol (0.5 mL). The resulting mixture was then stirred for 12 h (LC-MS check, molecular ion peak at 789 (M+H)$^+$) and rotovapped. The mixture of resulted 2-((S)-pyrrolidin-2-yl)-5-{6-([2-((S)-pyrrolidin-2-yl)-1H-imidazol-5-yl]buta-1,3-diynyl)thieno[3,2-b]thiophen-3-yl}-1H-imidazole tetrahydrochloride, N-Moc-L-valine (14.2 mg, 0.081 mmol) and HATU (35 mg, 0.092 mmol) in DMF (1.5 mL) was stirred in a fridge for 0.5 h, then DIPEA (24 mg, 0.185 mmol, 0.032 mL) was added, and the resulting mixture was continuously stirred in a fridge for 2 h. The mixture was diluted with 20 mL of DCM, washed twice with a 5% Na$_2$CO$_3$ solution, dried over Na$_2$SO$_4$, rotovapped and subjected to HPLC to obtain 7.4 mg (26%) of methyl (S)-1-[(S)-2-(5-{6-[(2-{(S)-1-[(S)-2-(methoxy carbonylamino)-3-methylbutanoyl]pyrrolidin-2-yl}-1H-imidazol-5-yl)buta-1,3-diynyl]thieno[3,2-b]thiophen-3-yl}-1H-imidazol-2-yl)pyrrolidin-1-yl]-3-methyl-1-oxo-butan-2-ylcarbamate dihydrochloride (1.10). The LC-MS molecular ion peak was at 773 (M+H)$^+$.

Example 7

Preparation of pharmaceutical composition in the form of tablet. Starch (1600 mg), ground lactose (1600 mg), talk (400 mg) and NS5A inhibitor 1.1 (1000 mg) were mixed together. The resultant bar was comminuted into granules and sifted through sieve to collect granules of 14-16 mesh. The granules thus obtained were shaped into tablets of suitable form weighing 560 mg each.

Example 8

Preparation of pharmaceutical composition in the form of capsules. NS5A inhibitor 1.1 and lactose powder were carefully mixed in ratio 2:1. The resultant powdery mixture was packed into gelatin capsules of suitable size by 300 mg to a capsule.

Example 9

Preparation of pharmaceutical composition in the form of injectable compositions for intramuscular, intraperitoneal or hypodermic injections. NS5A inhibitor 1.1 (500 mg), chlorobutanol (300 mg), propylene glycol (2 ml), and injectable water (100 ml) were mixed together. The resultant solution was filtered and placed into 1 ml ampoules, which were sealed.

INDUSTRIAL APPLICABILITY

The invention could be used in medicine, veterinary, biochemistry.

The invention claimed is:

1. Substituted azoles of formula 1A and pharmaceutically acceptable salts thereof,

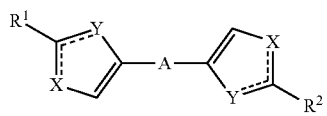

1A wherein:
solid lines with accompanying dotted lines (---) represent a single bond or a double bond, provided that if one of them is a single bond, then the other one is a double bond;
X and Y have optionally different meanings and represent nitrogen atom, or a NH group;
$R^1$ and $R^2$—represent optionally identical radicals 2.1-2.4, wherein an asterisk (*) denotes the position of attachment to the azolic fragment;

2.1

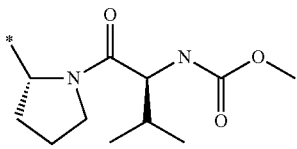

2.2

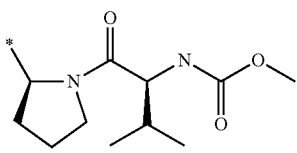

2.3

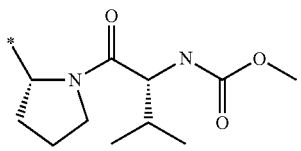

2.4

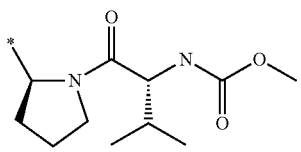

A represents:
biradical selected from biradicals of formulae 3.96, 3.100, wherein an asterisk (*) denotes the positions of attachment to the azolic fragments;

3.96

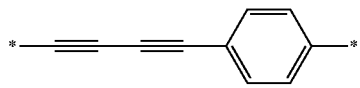

3.100

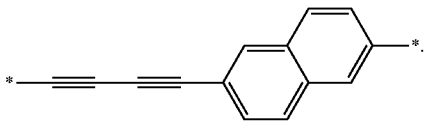

2. Compounds representing [(S)-1-((S)-2-{5-[4-(4-{2-[(S-1-((S-2-Methoxycarbonylamino-3-methyl-butyryl)-pyrrolidin-2-yl]-3H-imidazol-4-yl}-buta-1,3-diynyl)-phenyl]-1H-imidazol-2-yl}-pyrrolidine-1-carbonyl)-2-methyl-propyl]-carbamic acid methyl ester of formulae 14 and pharmaceutically acceptable salts thereof

14

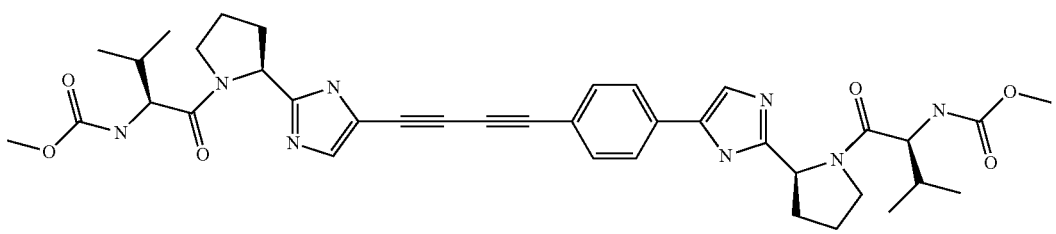

and [(S)-1-((S)-2-{5-[6-(4-{2-[(S-1-((S-2-Methoxycarbonylamino-3-methyl-butyryl)-pyrrolidin-2-yl]-3H-imidazol-4-yl}-buta-1,3-diynyl)-naphthalen-2-yl]-1H-imidazol-2-yl}-pyrrolidine-1-carbonyl)-2-methyl-propyl]-carbamic acid methyl ester of formulae 19 and pharmaceutically acceptable salts thereof

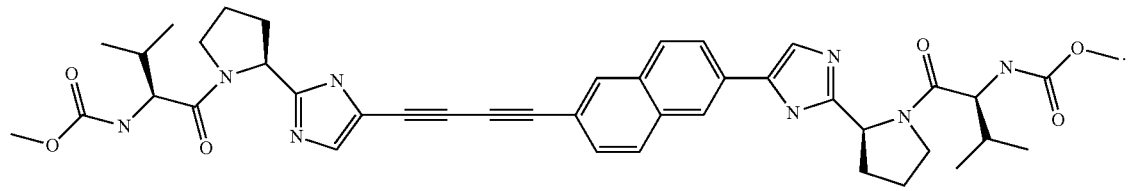

19

3. Pharmaceutical composition comprising an anti-hepatitis C virus effective amount of compounds according to claims 1 or 2.

* * * * *